US006325788B1

(12) United States Patent
McKay

(10) Patent No.: US 6,325,788 B1
(45) Date of Patent: Dec. 4, 2001

(54) TREATMENT OF WOUND OR JOINT FOR RELIEF OF PAIN AND PROMOTION OF HEALING

(76) Inventor: Douglas William McKay, 450 Moosa Blvd., Suite C, Eunice, LA (US) 70535

( * ) Notice: Subject to any disclaimer, the term of this patent is extended or adjusted under 35 U.S.C. 154(b) by 0 days.

(21) Appl. No.: 09/154,520

(22) Filed: Sep. 16, 1998

(51) Int. Cl.[7] .................................................. A61M 31/00
(52) U.S. Cl. ........................ 604/506; 604/540; 604/541; 604/543; 604/500; 604/27; 604/30; 604/120
(58) Field of Search .................................. 604/48, 4, 43, 604/500, 505, 131, 173, 284, 541, 543, 506, 4.01, 5.01, 30, 6.1, 7, 319, 119, 120

(56) References Cited

U.S. PATENT DOCUMENTS

| 3,142,298 | | 7/1964 | Koski et al. . |
| 3,771,527 | | 11/1973 | Ruisi . |
| 3,885,567 | | 5/1975 | Ross . |
| 3,885,590 | * | 5/1975 | Ford ........................................ 604/26 |
| 3,982,540 | * | 9/1976 | Ross ....................................... 604/540 |
| 4,443,220 | | 4/1984 | Hauer et al. . |
| 4,637,814 | * | 1/1987 | Leiboff ................................... 604/814 |
| 4,650,462 | * | 3/1987 | DeSatnick et al. ..................... 604/30 |
| 4,722,734 | | 2/1988 | Kolln . |
| 4,755,168 | | 7/1988 | Romanelli et al. . |
| 4,795,424 | | 1/1989 | Burner . |
| 4,850,969 | * | 7/1989 | Jackson .................................. 604/96 |
| 4,878,894 | * | 11/1989 | Sutter, Jr. et al. ...................... 604/34 |
| 5,002,528 | | 3/1991 | Palestrant . |
| 5,015,236 | * | 5/1991 | Lewis .................................... 604/120 |
| 5,078,704 | * | 1/1992 | Wejnar .................................. 604/317 |
| 5,120,312 | | 6/1992 | Wigness et al. . |
| 5,254,083 | | 10/1993 | Gentelia et al. . |
| 5,279,550 | | 1/1994 | Habib et al. . |
| 5,330,424 | | 7/1994 | Palmer et al. . |
| 5,599,308 | * | 2/1997 | Krupa .................................... 604/118 |
| 5,616,121 | * | 4/1997 | McKay ................................... 604/35 |
| 5,645,540 | * | 7/1997 | Henninges et al. ................... 604/320 |
| 5,662,135 | * | 9/1997 | Oppmann et al. ..................... 137/1 |
| 5,865,764 | * | 2/1999 | Moorhead ............................. 600/561 |

FOREIGN PATENT DOCUMENTS

| 1029624 | 4/1978 | (CA) . |
| 0 389 818 B1 | 10/1990 | (EP) . |
| 0 401 016 A1 | 12/1990 | (EP) . |
| 0 513 858 A2 | 11/1992 | (EP) . |
| 74.05574 | 2/1974 | (FR) . |
| 1 451 418 | 10/1976 | (GB) . |
| 2 26 0165 A | 9/1993 | (GB) . |
| WO 86/01412 | 3/1986 | (WO) . |
| WO 87/00759 | 2/1987 | (WO) . |
| WO 91/12830 | 9/1991 | (WO) . |

* cited by examiner

Primary Examiner—Anhtuan T. Nguyen
Assistant Examiner—Jennifer Maynard
(74) Attorney, Agent, or Firm—McDermott, Will & Emery

(57) ABSTRACT

Apparatus and method for treating a body joint wound subsequent to surgical intervention. An infusion tube is insertable into the wound for transporting a prepared solution to the joint. A second tube is insertable into the wound for transport of fluid removed from the joint. A vacuum device is coupled to the second tube. Suction is automatically turned on to evacuate the wound for a prescribed period of time and then stopped for another prescribed period of time. The on and off cycle may be repetitive. During the entire period, the prepared solution is constantly infused. The infusion tube and evacuation tube are isolated from each other so that no contaminants can be infused. A plurality of preadjusted suction duty cycles are available, from which one may be selected as appropriate for the type of wound to be treated.

17 Claims, 5 Drawing Sheets

TREATMENT OF WOUND OR JOINT FOR RELIEF OF PAIN AND PROMOTION OF HEALING

CROSS-REFERENCE TO RELATED APPLICATIONS

This is application is related to U.S. Pat. No. 5,616,121, issued to Douglas W. McKay Apr. 1, 1997.

TECHNICAL FIELD

The present invention relates to the treatment of a wound or joint, with particular applicability to post operative closed muscular skeletal wounds. The invention provides alleviation of pain, while promoting healing of the wound and early rehabilitation.

BACKGROUND OF THE INVENTION

Of major concern in the care of wounds such as incurred in joint surgery are relief of post-operative pain, avoidance of infection, hastening of healing and early joint motion, and decrease in the length of the patient hospital stay. Traditional post-operative management of orthopaedic wounds or traumatic wounds have varied in approach whereby wounds are left open or closed, with or without drains to drain out the debris and blood. Debris and blood are an excellent culture medium which is easily contaminated in dependence upon the wound environment. Accumulation of fluid in the wound causes swelling, pain and delayed healing.

Treatment of pain relief by means of narcotics has drawbacks such as constipation, drowsiness, stasis pneumonitis, itching, vomiting, confusion and ataxia. Problems associated with epidural analgesia include itching, constipation, increased blood loss, severe ataxia and very expensive multiple injections. Thus, the need has existed for new and improved means for management of pain relief and maintenance of a sterile environment.

U.S. Pat. No. 5,616,121, issued to McKay on Apr. 1, 1997, discloses a treatment for alleviating pain in joint wounds through use of irrigation with a medicinal solution. Irrigation lessens the risk of infection and scar tissue that would otherwise occur from accumulated debris and fluid. The patented treatment provides an infusion tubing for infusing a prepared solution into the wound, and a suction tubing for suctioning fluids from the wound. The infusion tubing and suction tubing are joined to communicate with a single tube that is inserted in the wound. Through the use of valves and controlled pump operation, successive timed intervals of infusion and suction, separated by interruption intervals, bathing of the wound is achieved.

Important criteria for use of medical devices in post operative care management are the following. The risk to the health or well being of the patient should be insignificant. Any device that is connected internally to the patient to infuse or subtract fluid should be a closed, sterile system to prevent invasion of environmental contaminants. As patients should be ambulatory as early as possible to prevent deep vein thrombosis, the device should be portable, thereby permitting patient mobility. Mobility also enhances the prospects of early rehabilitation and shortened hospital stay.

While the above described McKay patent meets these criteria, it has been found through the present invention that significant additional improvement is obtainable. The use of separate infusion tubes and suction tubes in the patented method avoids the mixing of the infusion solution and the joint fluids in either of the tubes. The separation of infusion periods and suction periods by interrupted intervals, minimizes such mixing in the single insertion tube. The single insertion tube, however, does have the disadvantage that debris or bacteria remaining therein from a previous suction period may be readministered to the joint during the following infusion period. A further disadvantage is that the pressure in the joint is subject to relatively wide variation over the repeated processes of infusion, interruption and suction. Negative pressure is to be avoided as bacteria can be drawn into the wound along the drain and through the skin.

A desirable practice during surgery and its immediate aftermath is to collect patient blood loss for reinfusion into the body if necessary. Reinfusion of the patient's blood is a preferable alternative to transfusion of blood from an unknown donor. Apparatus for autotransfusion are disclosed, for example, in U.S. Pat. No. 4,443,220, issued to Hauer et al. on Apr. 17, 1984, and in U.S. Pat. No. 5,279,550, issued to Habib et al. on Jan. 18, 1994. For post-operative treatment of joint wounds, patient bleeding occurring during an initial period would be collected, to be followed by an extended period of irrigation treatment, such as the McKay patent approach, or other care management. The entire procedure would involve set up and application of a blood collection device exemplified by the above identified patents, removal of this device, and subsequent application of the McKay patent irrigation system. This procedure has the disadvantages of subjecting the patient to added discomfort in the exchange of medical devices, increased time required to administer the exchange while maintaining a sterile environment, and the expense of the two medical devices necessary to perform both functions.

The need therefore exists for a single medical device, such as that of the McKay patent, that can perform both a blood saving function and a wound irrigation function. Such an apparatus should assure that the collection and saving of blood is accomplished without damage to blood cells.

SUMMARY OF THE INVENTION

The present invention overcomes the aforementioned disadvantages in part by its ability to mimic the normal defense of the human body to invasion by foreign material. The body has a normal tissue tension of 10–15 mm/Hg. A break in the skin will lead to swelling and increased tissue pressure. All wounds leak extra cellular fluid after bleeding has stopped due to the tissue tension, or pressure, that increases with inflammation and swelling. The leaking of cellular fluid in a wound relieves inflammation, swelling and pain in all layers through to the skin, while tending to prevent foreign materials from entering the wound.

An advantage of the present invention is that post-operative joint wound care can be provided with the maintenance of a positive physiological pressure in the wound automatically by appropriate infusion and suction of medicinal fluid to alleviate pain and promote healing.

An additional advantage of the present invention is that a closed wound irrigation system is provided wherein all infusion tubing will transport only infusion solution so that there is no mixing with body fluid or residue removed from the wound. A highly sterile environment thus can be provided and maintained at the wound. A concomitant advantage is that, without the possibility of such mixing, medicated solution can be infused throughout the irrigation period, during which time suction can be intermittently applied. This feature adds the advantage of more a simplified control of the irrigation process than the earlier prior art method.

Yet another advantage of the present invention is that a single device is provided that is capable of performing both a blood collection and saving function and a wound irrigation function following surgery with a minimum of invasive administration.

Another advantage of the present invention is that the system is portable, allowing early mobility, of particular importance to patients recovering from surgery at leg joints.

These and other advantages are satisfied, at least in part, by the provision of an apparatus for treating a body joint wound subsequent to surgical intervention. An infusion tube is insertable into the wound for transporting a prepared solution to the joint. The prepared solution may contain prescribed amounts of local anesthetic, anti-inflammatory, anti-coagulant and antibiotics. A second tube is insertable into the wound for transport of fluid removed from the joint. The latter tube has perforations along the portion that is to be inserted in the wound to aid entry of the body fluids. A vacuum device is coupled to the second tube. Suction is automatically turned on to evacuate the wound for a prescribed period of time and then stopped for another prescribed period of time. The on and off cycle can be repeated, for example, over a twenty four to seventy two hour period. During the entire period, the prepared solution is constantly infused. The infusion tube and evacuation tube are isolated from each other so that no contaminants can be infused. The on/off oscillation of the suction provides the advantage of pain alleviation as the cycle intervals are preadjusted to maintain a positive physiological pressure in the wound. As a result, the infused medicated solution, which has permeated the wound, can seep through to the skin in a manner that mimics the natural healing process of the body. Seepage of the medicated solution greatly enhances the process of relieving swelling, inflammation and contamination. A plurality of preadjusted duty cycles are available, from which one may be selected as appropriate for the type of wound to be treated.

The vacuum device is a self-contained structure that includes a reservoir for receiving fluids evacuated from the wound and a section in which the vacuum apparatus and its control are housed. The reservoir is an enclosure having a top portion with two fluid inlet ports and a bottom portion having a fluid outlet port. The bottom portion is sloped to facilitate drainage of fluid collected in the enclosure through the outlet port. The two inlet ports are coupled respectively to two ends of a Y shaped portion of the second tube. The reservoir enclosure is structured to facilitate collection of blood received from one of the fluid input ports. An inverted cone-shaped configuration extends from the bottom portion of the reservoir to a location in close proximity to this port to spread the blood near the entry of the reservoir and prevent damage to the blood cells. A filter surrounds the cone-shaped structure for filtering out particles, such as clots, from the received blood. The blood saving function occurs in an initial period following surgery, after which period the tube coupled to the blood saving input port preferably is clamped shut. Collected blood is drained through the bottom output port. A vacuum release valve is provided at the top of the enclosure to preclude negative pressure in the reservoir while the blood is drained.

Preferably, the irrigation period then follows, the evacuated fluid being received through the other fluid input port. During the suction periods, negative pressure is created in the reservoir by a pump, which by way of example may be a commonly available battery powered reciprocating pump. Timed duty cycle operation for the pump preferably is under the control of a microprocessor circuit, which includes a plurality of manually selectable switch settings. The pump may be activated at one of a plurality of duty cycles or in a constant mode in response to a selected switch setting. A valve, located at the second reservoir fluid inlet port is actuatable during the pump operating periods to permit suction of the fluid from the evacuation tube entry to the reservoir. While the valve may be a pressure responsive valve, a solenoid valve is preferable as the latter permits a more direct control. By appropriate selection of the pump operating mode switch setting, a positive physiological pressure can be maintained at the joint wound while the medicated solution is constantly infused.

Additional advantages of the present invention will become readily apparent to those skilled in this art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF THE DRAWINGS

Reference is made to the attached drawings, wherein elements having the same reference numeral designations represent like elements throughout and wherein.

DETAILED DESCRIPTION OF THE INVENTION

Figure 1:
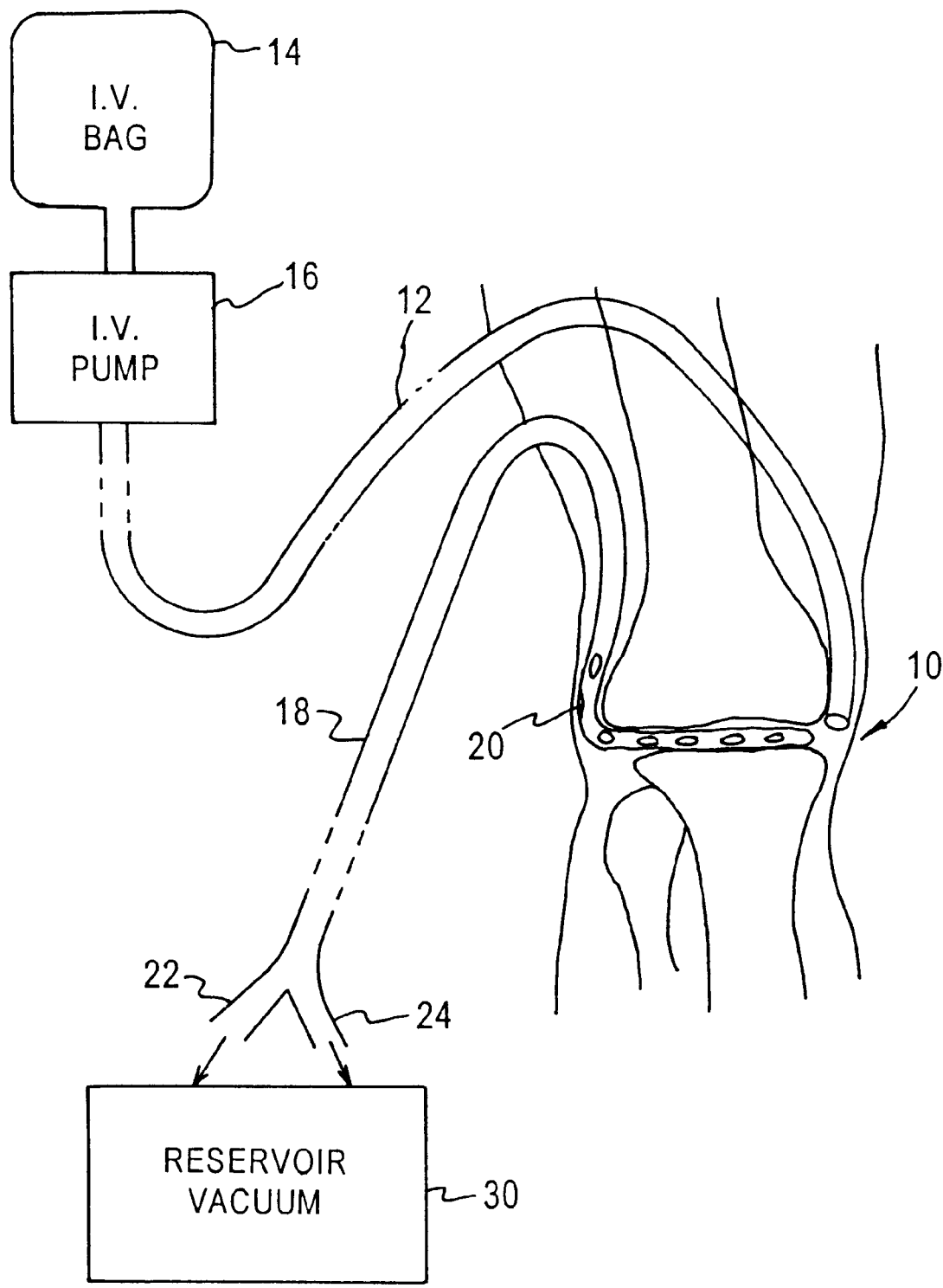
FIG. 1 is a simplified schematic diagram of a body joint wound treatment system in accordance with the present invention.
Figure 2:
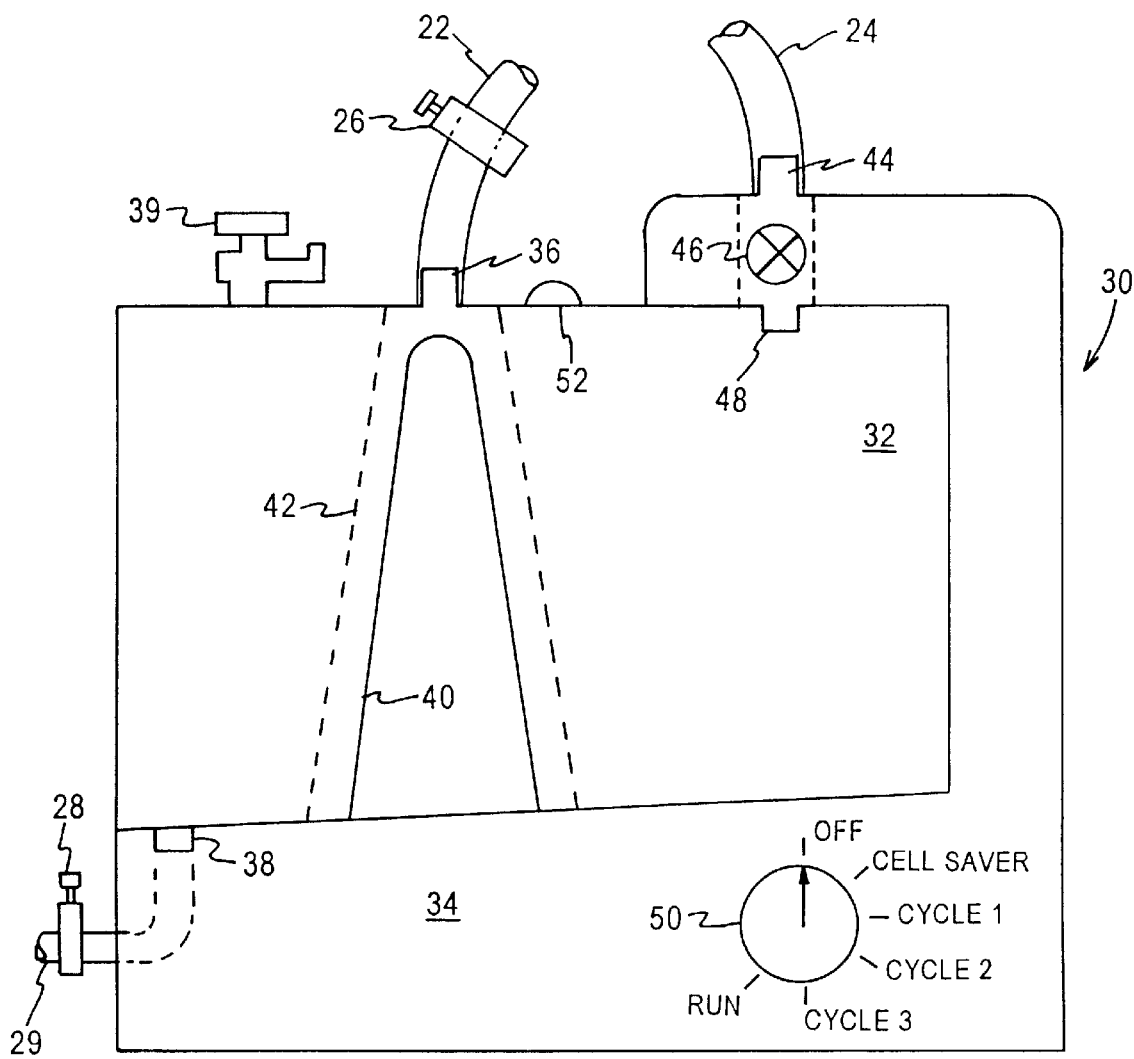
FIG. 2 is a more detailed front schematic view of the reservoir and vacuum device shown in FIG. 1.

FIG. 1 is illustrative of the system of the invention as applied to a wound in knee area 10. It is to be understood that the knee joint is shown only by way of example and that the invention also is intended to be used for other body joint wounds including, but not limited to, larger joints such as the hip and smaller joints such as wrists, elbows and ankles. Infusion tubing 12, shown inserted into the wound area, is fed a medicated solution from an I.V. source 14 through I.V. pump 16. The pump may be a standard commercially available device, such as manufactured for example, by Baxtor, I-VAC, Travenol, etc., and which is capable of providing pump rates at least within a range of 30 cc/hr. to 70 cc/hr. During the irrigation period, the solution preferably contains anesthetic, anti-inflammatory, anti-coagulant and antibiotic agents, for example, Lidocaine, Chloromycetin, Solu-Cortef and Heparin. When the system is used for a blood collection function, a small amount of saline may be used in solution to prevent blood clotting in the evacuation tubing 18. The evacuation tubing contains perforations in the end portion 20 that is shown inserted in the wound. Tubing 18 transports fluid from the wound to self contained reservoir and vacuum device 30 through Y shaped end portions 22 and 24 that are coupled to fluid input ports in the reservoir. The reservoir ports and other features of reservoir and vacuum device 30 are illustrated in the more detailed diagrams of FIGS. 2–4. FIG. 2 is a front perspective view of the reservoir and vacuum device structure 30, shown schematically. The structure comprises a fluid containing portion 32 and housing portion 34 in which the vacuum control apparatus is located. Container 32 preferably is made of transparent plastic material so that the level of the contents easily can be seen. Graduation marks, which can denote volume level, are shown along the left side of the container. The capacity of the reservoir preferably is of an order of 750 cc. The housing portion 34 preferably is made of opaque material that can be made, for example, by injection molding.

The end portion 22 of the evacuation tube 18 through which blood is transported is provided with a manually operable clamp 26. Portion 22 is coupled to fluid input port 36 on the top of the reservoir container 32. An additional clamp 28 is provided on tubing 29 that is coupled to a fluid exit port 38 in the bottom of the reservoir container. Pressure release valve 39 may be pushed when fluid is to be drained from the container through port 38. Valve 39 thus permits air to enter the container to equalize outside and inside pressures. A filter may be included to avoid entry of outside contaminants. Housing 34 contains a channel for passage of the tubing from port 38. The bottom of the container is sloped so that fluid readily can be fed by gravity flow to the exit port. Blood exiting the reservoir can be collected in a blood bag for reinfusion.

Inverted cone shaped structure 40 extends from the container bottom to a location proximate input port 36 at the top of the container. Blood entering therethrough will travel a short distance to the top of the cone and then down along the cone surface. The cone avoids damage to the blood cells that might otherwise occur if the blood were to traverse the entire distance in free fall. In the latter case, splattering or splashing is likely to occur, causing air to break up the cells. Filter 42, which surrounds the cone between the top and bottom of the container precludes passage of particles, such as clots or debris, therethrough to the reservoir.

Port 38, tubing 29 and clamp 28 also provide a means for draining the container of irrigation fluids transported from the wound. End portion 24 of the evacuation tube 18 is coupled to fluid input port 44 at the top of the reservoir housing 34. Structurally aligned in a vertical direction with port 44 are valve 46 and port 48. Valve 46, preferably a spring loaded solenoid valve, is operable to an open position to permit the flow of fluid from tube portion 24 to the container 32 during the irrigation suction intervals. A pressure transducer in tubing 24 will electrically open the solenoid if pressure exceeds an A.A.B.B. prescribed limit.

Manually operable switch knob 50, which protrudes from the front of housing 34, can be set to one of several cycle operating mode positions or off and continuous run modes. Vacuum indicator 52 provides a visual indication of a vacuum condition. This device may comprise a transparent window to the periphery of which is sealed a flexible material. A vacuum level in the container sufficient for operation in a selected suction mode will cause an inward deflection of the material that is visibly recognizable from outside the reservoir container.

Figure 3:
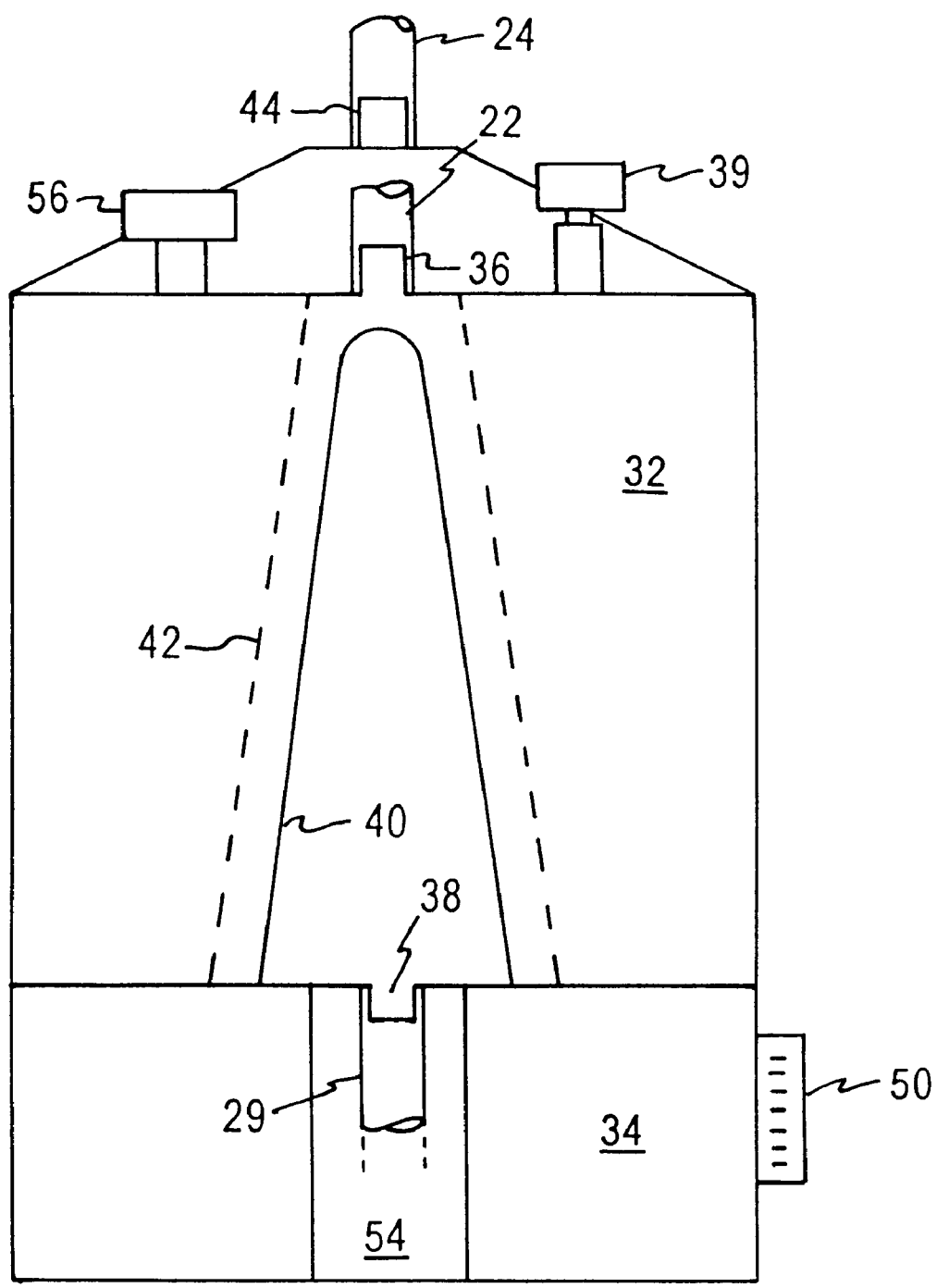
FIG. 3 is a left side schematic view of the reservoir and vacuum device.

FIG. 3 is a left side schematic view of the reservoir and vacuum device. Housing 34 contains a channel 54, recessed from its outer edge for passage of the tubing 29 from port 38. The channel, which extends to the bottom of housing 34, permits the tubing to emerge from the left side of the housing, as depicted in FIG. 2, or from the bottom. The device 30 thus can be placed on a horizontal surface or carried as the rehabilitating patient becomes mobile. A clip, not shown, may be attached to the housing for hanging from a hospital railing or the like. Port 56 permits connection of the reservoir to an alternative vacuum source, such as a wall source, common to hospital rooms. The port is provided with a cap and check valve to prevent entry of air into the reservoir.

Figure 4:
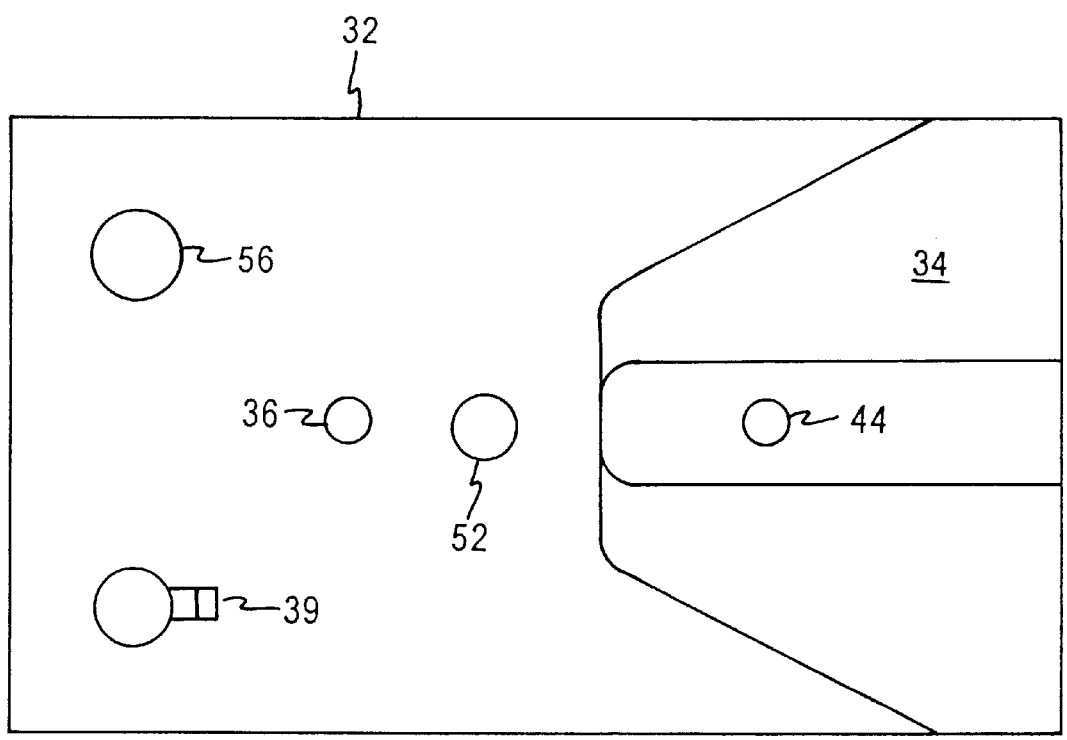
FIG. 4 is top schematic view of the reservoir and vacuum device.

FIG. 4 is a top view of the reservoir and vacuum device housing, illustrating the relative positions of the various elements previously described.

Figure 5:
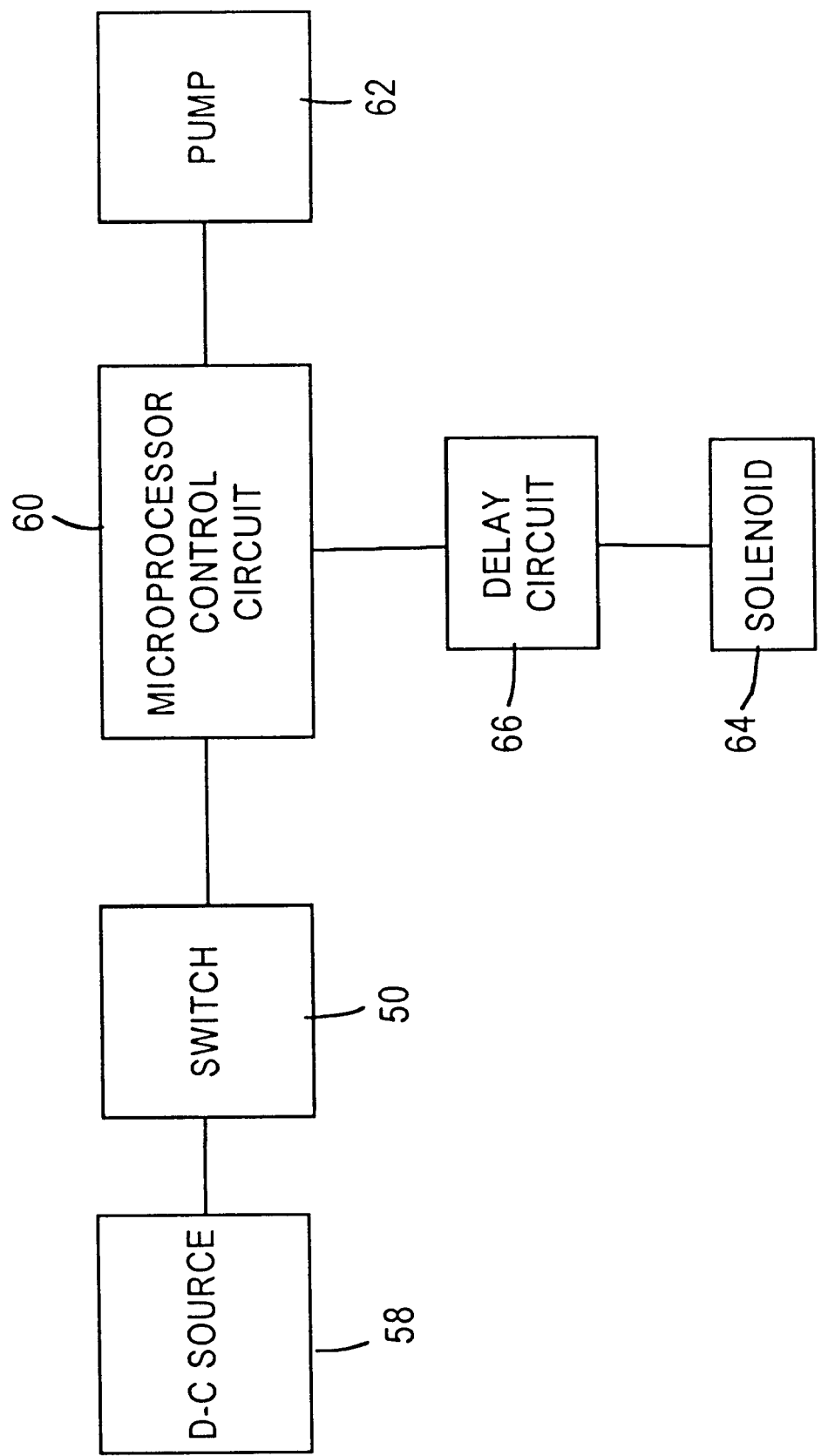
FIG. 5 is a simplified block diagram of a preferred control scheme in accordance with the present invention.

FIG. 5 is a simplified block diagram of a preferred control scheme of the vacuum device of the present invention that is contained in housing 34. Switch 50 is connected between d-c source and control circuit 60. Control circuit 60 preferably comprises a commercially available microprocessor timing circuit. While a single line is shown in the block diagram, it is to be understood that a plurality of connections are made from the various switch contact settings, illustrated in FIG. 2, to appropriate inputs of the microprocessor. The microprocessor provides control output signals to pump 62 and solenoid 64, the latter through delay circuit 66. Pump 62, when activated, creates the vacuum condition in the reservoir. Solenoid 64 is operative to control valve 46 at the input port 44 in housing 34. The time delay circuit may be of conventional design, such as a resistor-capacitor arrangement.

The plurality of switch positions correspond to the "OFF," "Cell Saver (CS)", "Cycle 1," "Cycle 2," "Cycle 3" and "Run" designations shown in FIG. 2. The "Run" setting represents continuous running operation. Except for the "OFF" condition, the other settings represent different on/off modes having respective duty cycles and cycle times. By way of example, the following table indicates preferred setting values.

| Mode | Suction On | Suction Off | Cycle Time |
| --- | --- | --- | --- |
| CS | 05 minutes | 25 minutes | 1/2 hour |
| 1 | 10 minutes | 50 minutes | 1 hour |
| 2 | 20 minutes | 100 minutes | 2 hours |
| 3 | 30 minutes | 150 minutes | 3 hours |

In preferred operation, the CS (cell saver) mode is used immediately after surgery while the patient is losing at least 80 ccs per hour without evidence of large clots. This mode can be in place for about ten hours, while a solution containing heparin and saline is infused to minimize blood clotting. In this mode the switch is set to the CS setting, whereby the microprocessor control circuit outputs a repetitive on/off duty cycle such as indicated in the table for CS. Clamp 26 will be manually opened. The solenoid will not be activated during this cycle as there is no connection therefrom to the CS switch contact. The fluid from the wound therefore will gain entry to the reservoir only at the input port 36. Blood entering the reservoir will impinge on the cone structure 40 and then traverse through by filter 42. Blood collected in the reservoir can be drained when the contents reach a desired volume level, which can be observed through the clear reservoir container. Drainage is achieved by manually operating pressure release valve 39 and opening clamp 28. Tubing 29 can be coupled at this time to a blood bag to be used for reinfusion. Thereafter, blood collection can continue in the CS mode, with the clamp 28 closed and the pressure release valve inactive.

The blood collection period will continue until the physician determines that bleeding has sufficiently diminished. Thereafter, the switch is set to one of the preset irrigation cycle settings (1–3) in accordance with what the physician deems appropriate for the type of wound being treated. At the outset of the selected cycle, the control circuit will output signals representing an on condition for the pump. In response, power is supplied to the pump which creates a vacuum in the reservoir. The appropriate vacuum level is designed to allow a maximum of approximately 100 mm/Hg pressure, a level that conforms with A.A.B.B (American Association of Blood Banks) finding as to safety and comfort. Pressure is related to several variables including infusion rate, the length of tubing, the height of the vacuum source with respect to the level of the knee or other joint being treated. These factors would all be taken into consideration by the artisan in determining the precise pump capacity and timed intervals. Activation of solenoid 64 may be delayed from the initial switch setting for the cycle by delay circuit 66. The delay permits a sufficient vacuum to be established by pump 62 in the reservoir before the valve 46 will be opened to provide transport of the fluid from tube 24 to the reservoir container. Thereafter, the solenoid is activated and remains in this condition during the suction interval. The microprocessor control circuit will time out the suction on interval and then change the output control signals to deactivate the pump and solenoid for the timed suction off interval. This cyclic operation is repeated until the switch is set to the OFF position. Operation would occur in a similar manner for each of the other cycle modes.

In an alternative operative embodiment, the controlled vacuum in the reservoir can be constantly maintained at the appropriate level, i.e. approximately 100 mm/Hg, by use of a small vacuum pump and pressure transducer. The pump can be powered by battery, a-c or converted a-c. In this embodiment, the microprocessor will cyclically operate the solenoid in each of the selected mode cycles, without delay. As the desired pressure in the reservoir is maintained relatively constant, the delay circuit 66 can be eliminated or adjusted to zero delay.

A significant aspect of the present invention is that a positive pressure is maintained in the joint to cause the wound and the area around the tubes to allow the fluid to escape from the joint through the skin. This seepage keeps the bacteria count down in the wound and on the skin around the wound. Seepage not only cleans and relieves pain to the multiple layers of the wound and skin, but serves as a control valve maintaining a physiologically comfortable pressure in wound area. The amount of seepage can be detected visually by inspection of the wound dressings. If the dressing appears too dry, the infusion rate can be increased an incremental amount, for example, by 10 cc/hour. If seepage appears too heavy, diminishment of the infusion rate by a similar amount would be appropriate. These adjustments may easily be implemented.

It can be appreciated that the present invention provides the advantage of portability because the device can be light weight, battery powered and self contained. In periods in which the patient is not mobile, battery power can be saved by use of an a-c power supply with appropriate converter.

In this disclosure there is shown and described only the preferred embodiments of the invention and but a few examples of its versatility. It is to be understood that the invention is capable of use in various other combinations and environments and is capable of changes or modifications within the scope of the inventive concept as expressed herein. For example, while the preferred embodiment has been described as applicable to various surgical joint wounds, the invention would have use in other body wounds with minor modifications that would be within the skill of the practitioner.

What is claimed is:

1. A method for automatically treating a body joint wound subsequent to surgical intervention comprising the steps of:
    providing an apparatus for treating a wound at a body joint subsequent to surgical intervention, said apparatus comprising:
    a first tube insertable into said wound for transporting an infused solution to said body joint, said first tube being connectable to a source of said solution;
    a second tube insertable into said wound for transport of fluid removed from said body joint;
    a vacuum device coupled to said second tube, said vacuum device comprising:
        a valve located in proximity to an end of said second tube at which said vacuum device is coupled at an inlet port;
        a reservoir for receiving fluid transported from said body joint through said second tube and said valve;
        a pump for creating a pressure in said reservoir that is negative with respect to pressure within said second tube; and
        a controller for periodically activating said pump at preset time intervals while said solution is being infused to said body joint;
    wherein a relatively constant positive physiological pressure is maintained in the joint during and throughout a solution infusion period;
    wherein said second tube contains a Y section comprising an input portion receiving the transported fluid from the body joint and two output portions, a first of said output portions being coupled to said inlet port; and
    a second of said output portions coupled to a second inlet port at said reservoir;
    continuously infusing a solution into the joint at a relatively constant rate; and
    maintaining a relatively constant positive physiological pressure in the joint during and throughout said infusing step.

2. A method as recited in claim 1, wherein said pressure is of a level to enable permeation of fluid from the joint to the skin surface of the wound and seepage therethrough, whereby swelling of the wound area is minimized and early healing is promoted.

3. A method as recited in claim 1, wherein said maintaining step comprises the step of:
    periodically suctioning fluid from the joint for preset time intervals while said solution is being infused in said infusing step.

4. A method as recited in claim 3, wherein said infusing step comprises inserting said first tube in said wound for transporting the infused solution to the joint, and said maintaining step further comprises inserting said second tube in said wound for transport of said fluid from the joint in said suctioning step.

5. A method as recited in claim 4, wherein said solution comprises one or more elements of the group consisting of an analgesic agent, an anti-coagulant agent and an antibacterial agent, and wherein said pressure is of a level to permit permeation of said solution from the joint to the skin surface of the wound and seepage therethrough, thereby minimizing swelling of the wound area, diminishing pain, and promoting early healing.

6. A method as recited in claim 4, wherein said suctioning step comprises the steps of:

adjusting the length of said preset time intervals in accordance with physiological factors among which are included the size of the wound; and applying a relatively constant negative pressure to said second tube during each said preset time interval.

7. Apparatus for treating a wound at a body joint subsequent to surgical intervention, said apparatus comprising:

a first tube insertable into said wound for transporting an infused solution to said body joint, said first tube being connectable to a source of said solution;

a second tube insertable into said wound for transport of fluid removed from said body joint;

a vacuum device coupled to said second tube, said vacuum device comprising:

a valve located in proximity to an end of said second tube at which said vacuum device is coupled at an inlet port;

a reservoir for receiving fluid transported from said body joint through said second tube and said valve;

a pump for creating a pressure in said reservoir that is negative with respect to pressure within said second tube; and a controller for periodically activating said pump at preset time intervals while said solution is being infused to said body joint;

wherein a relatively constant positive physiological pressure is maintained in the joint during and throughout a solution infusion period;

wherein said second tube contains a Y section comprising an input portion receiving the transported fluid front the body joint and two output portions, a first of said output portions being coupled to said inlet port; and a second of said output portions coupled to a second inlet port at said reservoir.

8. Apparatus as recited in claim 7, wherein said controller comprises a plurality of switch settings that correspond to respective unique timing cycles, each timing cycle comprising a specified activation time period length and inactivation time period length; and a timer circuit operative in response to a selected one of said switch settings to establish pump operation in accordance with the timing cycle corresponding to the selected setting.

9. Apparatus as recited in claim 8, wherein said timer circuit comprises a microprocessor.

10. Apparatus as recited in claim 7, wherein said reservoir comprises an enclosure having a top portion containing both of said inlet ports and a bottom portion containing an outlet port, said bottom portion being sloped to facilitate drainage of fluid in said enclosure through said outlet port.

11. Apparatus as recited in claim 10, wherein said top portion further comprises a vacuum indicator.

12. Apparatus as recited in claim 10, wherein said reservoir comprises blood collecting means for collecting blood from the joint wound without damaging blood cells for reinfusion into the body.

13. Apparatus as recited in claim 12, wherein said blood is received at said second inlet port, and said blood collecting means comprises:

an inverted cone-shaped structure extending from the bottom portion of the reservoir to a location in close proximity to said second inlet port for receiving blood from said second inlet port; and a filter surrounding said cone-shaped structure for filtering the blood received from said second inlet port;

and the second output portion of said Y section comprises a clamp for regulating flow therethrough.

14. Apparatus as recited in claim 10, wherein the top portion of the reservoir comprises a third inlet port for connection to an auxiliary vacuum source.

15. Apparatus as recited in claim 10, wherein said reservoir further comprises vacuum release means for permitting filtered air entry to said enclosure.

16. Apparatus as recited in claim 7, wherein said second tube comprises perforations distributed along a portion insertable into the joint.

17. Apparatus as recited in claim 7, wherein said valve is a solenoid valve.

* * * * *